United States Patent [19]

Ramey et al.

[11] 4,203,890
[45] * May 20, 1980

[54] HINDERED PIPERIDINE CARBOXYLIC ACIDS, METAL SALTS THEREOF AND STABILIZED COMPOSITIONS

[75] Inventors: Chester E. Ramey, Spring Valley; John L. Luzzi, Carmel, both of N.Y.

[73] Assignee: Ciba-Geigy Corporation, Ardsley, N.Y.

[*] Notice: The portion of the term of this patent subsequent to Nov. 18, 1992, has been disclaimed.

[21] Appl. No.: 910,553

[22] Filed: May 30, 1978

Related U.S. Application Data

[62] Division of Ser. No. 671,910, Mar. 29, 1976, Pat. No. 4,101,509.

[51] Int. Cl.² ............... C08K 5/34; C07D 211/46
[52] U.S. Cl. ....................... 260/45.8 N; 546/188; 546/205
[58] Field of Search ............... 260/293.81, 293.88, 260/45.8 N

[56] References Cited

U.S. PATENT DOCUMENTS

| | | | |
|---|---|---|---|
| 3,120,540 | 2/1964 | Meltzer et al. | 260/293.63 |
| 3,907,803 | 9/1975 | Ramey et al. | 260/45.8 NP |
| 3,920,661 | 11/1975 | Ramey et al. | 260/45.8 NP |
| 3,960,809 | 6/1976 | Ramey et al. | 260/45.8 NP |
| 4,031,095 | 6/1977 | Ramey et al. | 260/45.8 NP |
| 4,056,507 | 11/1977 | Ramey et al. | 260/45.8 NP |
| 4,069,199 | 1/1978 | Ramey et al. | 260/45.8 NP |
| 4,089,842 | 5/1978 | Ramey et al. | 260/45.8 NP |
| 4,101,508 | 7/1978 | Minagawa et al. | 260/45.8 NP |
| 4,101,509 | 7/1978 | Ramey et al. | 260/45.8 NP |
| 4,116,927 | 9/1978 | Minagawa et al. | 260/45.8 NP |
| 4,116,933 | 9/1978 | Ramey et al. | 260/45.8 NP |

Primary Examiner—V. P. Hoke
Attorney, Agent, or Firm—Vincent J. Cavalieri; Luther A. R. Hall

[57] ABSTRACT

Compounds having the formula

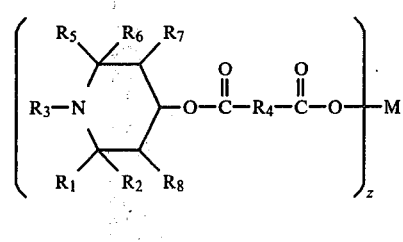

wherein $R_1$ and $R_2$ are lower alkyl or together lower alkylene,
$R_3$ is hydrogen, alkyl, methoxyethyl, alkenyl, propargyl, benzyl, alkyl substituted benzyl, or acyl,
$R_4$ is alkylene of 1 to 4 carbon atoms substituted with alkyl or alkenyl of 1 to 18 carbon atoms, alkenylene of 1 to 4 carbon atoms, cycloalkylene, cycloalkenylene, bicycloalkylene, bicycloalkenylene, or phenylene,
M is hydrogen or a metal, and
z has a value of from 1 to 4, and either (a) $R_5$ is alkyl of 1 to 6 carbon atoms, $R_6$ is alkyl of 1 to 6 carbon atoms, and $R_7$ and $R_8$ are independently hydrogen or alkyl of 1 to 5 carbon atoms, provided that $R_7$ and $R_8$ are not both hydrogen, or (b) $R_5$ and $R_6$ are together lower alkylene and $R_7$ and $R_8$ are independently hydrogen or alkyl of 1 to 5 carbon atoms, are good light stabilizers. The carboxylic acids are prepared for example, from 2,3,6-trimethyl-2,6-diethyl-piperidin-4-ol and 1,2-cyclohexanedicarboxylic anhydride to give 2,3,6-trimethyl-2,6-diethyl-4-piperidyl hydrogen 1,2-cyclohexanedicarboxylate. The metal salts of the acids are readily prepared by reacting the acids or their salts with a reactive form of the metal or metal complex.

12 Claims, No Drawings

HINDERED PIPERIDINE CARBOXYLIC ACIDS, METAL SALTS THEREOF AND STABILIZED COMPOSITIONS

This is a divisional of application Ser. No. 671,910, filed on Mar. 29, 1976, now U.S. Pat. No. 4,101,509.

BACKGROUND OF THE INVENTION

This invention relates to the stabilization of organic material normally tending to deteriorate. In particular, the invention relates to the protection of synthetic polymers against the harmful degradative effects, such as discoloration and embrittlement, caused by exposure to light, especially ultraviolet light.

It is known that actinic radiation, particularly in the near ultraviolet region, has a deleterious effect on both the appearance and properties of organic polymers. For example, normally colorless or light colored polyesters yellow on exposure to sunlight as do such cellulosics as cellulose acetate. Polystyrene discolors and cracks, with accompanying loss of its desirable physical properties when exposed to actinic light, while vinyl resins, such as polyvinyl chloride and polyvinyl acetate, spot and degrade. The rate of air oxidation of polyolefins, such as polyethylene and polypropylene, is materially accelerated by ultraviolet light.

In U.S. Pat. No. 3,120,540 there is discussed the reaction of substituted 4-piperidinol compounds with acid anhydrides having formula

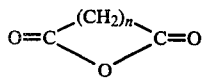

where n is 1 to 4, to yield bis(polymethyl)-4-piperidyl alkanoates. In the example of this patent the salt of 1,2,2,6,6-pentamethyl-4-piperidinol with the acid of formula

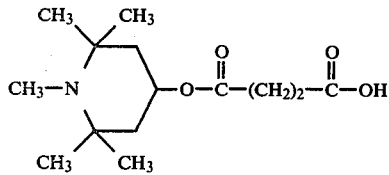

is a plausible intermediate in the synthesis of the bis(hydrogen sulfate)salt of bis(1,2,2,6,6-pentamethyl-4-piperidyl)succinate. The compounds of U.S. Pat. No. 3,120,540 are taught to possess significant pharmacological activity in lowering blood pressure. We have now found that acid half esters of hindered piperidines stabilize organic substrates against the degradative effect of ultraviolet light.

DETAILED DISCLOSURE

The present invention is accordingly directed to a new class of ultraviolet light stabilizers which consists of a compound of the formula

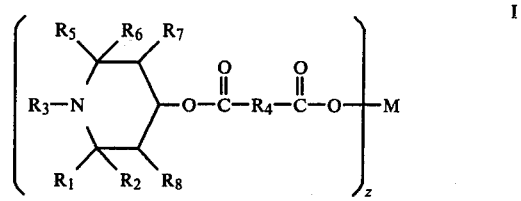

wherein
$R_1$ and $R_2$ independently of each other are straight- or branched-chain alkyl having from 1 to 6 carbon atoms, or together with the carbon to which they are bound form a cyclopentyl or cyclohexyl ring, which is unsubstituted or substituted with a methyl group, $R_3$ is hydrogen, alkyl having 1 to 12 carbon atoms, $\beta$-methoxyethyl, alkenyl having 3 to 4 carbon atoms, propargyl, benzyl, alkyl substituted benzyl or acyl, $R_4$ is straight-chain alkenylene of 2 to 4 carbon atoms, 1,2-cycloalkylene or 1,2-cycloalkenylene having 4 to 6 carbon atoms, 2,3-bicycloalkylene or 2,3-bicycloalkenylene having 7 or 8 carbon atoms or 1,2-, 1,3-, or 1,4-phenylene or straight-chain alkylene of 1 to 4 carbon atoms subtituted by alkyl or alkenyl of 1 to 18 carbon atoms, provided that said straight-chain alkylene substituted by alkyl has in total more than 8 carbon atoms, M is hydrogen or a metal selected from the group consisting of barium, nickel, manganese, calcium, copper, zinc, magnesium, sodium, potassium, cobalt, tin, and dialkyl tin z has a value of from 1 to 4, the value of z being the same as the available valence of M, and either (a) $R_5$ is alkyl of 1 to 6 carbon atoms, preferably 2 to 6 carbon atoms, $R_6$ is alkyl of 1 to 6 carbon atoms, and $R_7$ and $R_8$ are independently hydrogen or alkyl of 1 to 5 carbon atoms, provided that $R_7$ and $R_8$ are not both hydrogen, or (b) $R_5$ and $R_6$ together with the carbon to which they are bound form a cyclopentyl or cyclohexyl ring, which is unsubstituted or substituted with a methyl group and $R_7$ and $R_8$ are independently hydrogen or alkyl of 1 to 5 carbon atoms.

Examples of $R_1$ and $R_2$ are methyl, ethyl, n-propyl, n-butyl and n-hexyl. Preferably, $R_1$ and $R_2$ are each lower alkyl such as a methyl group. Representative of $R_1$ and $R_2$ together with the carbon to which they are bound as cycloalkyl groups are cyclohexyl, cyclopentyl, 2-methyl-, 3-methyl- and 4-methylcyclohexyl, and 2-methyl- and 3-methylcyclopentyl. The preferred cycloalkyl groups are cyclohexyl and 2-methylcyclohexyl. Most preferably, $R_1$ is methyl and $R_2$ is ethyl.

Substituent $R_3$ can be hydrogen, alkyl having 1 to 12 carbon atoms, preferably alkyl having 1 to 4 carbon atoms, hydrogen and methyl being particularly preferred, $\beta$-methoxyethyl, alkenyl having 3 to 4 carbon atoms, preferably allyl, propargyl, benzyl or alkyl substituted benzyl. Acyl $R_3$ is especially alkanoyl with 1 to 18, especially 2 to 6 carbon atoms, e.g., acetyl, or alkenoyl with 2 to 18 carbon atoms, especially 2 to 6 carbon atoms, e.g., acryloyl or crotonyl.

Examples of $R_3$ are hydrogen, methyl, ethyl, n-propyl, isopropyl, n-butyl, isobutyl, n-hexyl, n-octyl, n-dodecyl, allyl, $\alpha$-methallyl, propargyl, benzyl, $\alpha$-methylbenzyl and $\alpha$,p-dimethylbenzyl.

Examples of cyclic groups represented by $R_4$ are 1,2-cyclobutylene, 1,2-cyclohexylene, 4-cyclohexene-1,2-ylene, bicyclo[2,2,1]hept-2,3-ylene and bicyclo[2,2,2]oct-2,3-ylene, and especially bicyclo[2,2,1]hept-5-en-2,3-ylene and 1,2-phenylene.

Examples of acyclic groups represented by $R_4$ are octadecylethylene, dodecylethylene, octylethylene, 2-dodecenylethylene, 2-octenylethylene, 2-butenylene, vinylene, methyl-vinylene, octyl-vinylene and octadecyl-vinylene.

Among the substituents represented by M, hydrogen and nickel are preferred.

Examples of $R_5$ and $R_6$ are methyl, ethyl, n-propyl, n-butyl and n-hexyl.

Alkyl $R_5$ is especially n-alkyl of 2 to 6 carbon atoms, most preferably ethyl. Alkyl $R_6$ is especially n-alkyl with 1 to 6 carbon atoms, e.g., ethyl, most preferably methyl. Alkyl $R_7$ and $R_8$ are especially n-alkyl, like methyl, but most preferably one of $R_7$ and $R_8$ is hydrogen and the other one is methyl.

Most preferably $R_7$ contains one carbon atom less than $R_5$, and $R_8$ contains one carbon atom less than $R_6$. Also, most preferably, $R_1$ is the same as $R_5$ and $R_2$ is the same as $R_6$.

Representative of $R_5$ and $R_6$ together with the carbon to which they are bound as cycloalkyl groups are cyclohexyl, cyclopentyl, 2-methyl-, 3-methyl- and 4-methylcyclohexyl, and 2-methyl- and 3-methylcyclopentyl. The preferred cycloalkyl groups are cyclohexyl and 2-methylcyclohexyl.

A preferred group of compounds of formula I are therefore those wherein $R_1$ and $R_5$ are ethyl, $R_2$ and $R_6$ are methyl, one of $R_7$ and $R_8$ is hydrogen and the other is methyl, $R_3$ is hydrogen, methyl, allyl, benzyl, acetyl, acryloyl or crotonyl, and $R_4$, M and z have the above-preferred meanings.

Particularly preferred compounds of the invention have the formula

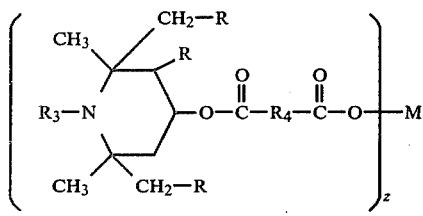

wherein R is lower n-alkyl of 1 to 5 carbon atoms, especially methyl, and $R_3$, $R_4$ and M are as defined above.

This invention also relates to compositions of matter which are stabilized against ultraviolet light deterioration which comprise a synthetic organic polymer normally subject to ultraviolet deterioration containing from about 0.005% to 5% by weight of the polymer of the compounds of formula I and preferably from 0.01 to 2% by weight.

The compounds as represented by formula I, can be used in combination with other light stabilizers such as 2(2-hydroxyphenyl)benzotriazoles, 2-hydroxybenzophenones, nickel complexes and benzoates.

The compounds of this invention are stabilizers for organic material normally subject to thermal, oxidative or actinic light deterioration. Materials which are thus stabilized include synthetic organic polymeric substances including homopolymers, copolymers, and mixtures thereof, such as vinyl resins formed from the polymerization of vinyl halides or from the copolymerization of vinyl halides with unsaturated polymerizable compounds, e.g., vinyl esters, $\alpha,\beta$-unsaturated acids, $\alpha,\beta$-unsaturated esters, $\alpha,\beta$-unsaturated ketones, $\alpha,\beta$-unsaturated aldehydes and unsaturated hydrocarbons such as butadienes and styrene; poly-$\alpha$-olefins such as high and low density polyethylene, crosslinked polyethylene, polypropylene, poly(4-methyl)-1-pentene and the like, including copolymers of $\alpha$-olefins; such as ethylene-propylene copolymers, and the like; polydienes such as polybutadiene, polyisoprene, and the like, including copolymers with other monomers; polyurethanes such as are prepared from polyols and organic polyisocyanates, and polyamides such as polyhexamethylene adipamide and polycarbonates such as those prepared from bisphenol-A and phosgene; polyacetals such as polyethylene terephthalate polyacetal; polystyrene, polyethyleneoxide; polyacrylics such as polyacrylonitrile; polyphenyleneoxides such as those prepared from 2,6-dimethylphenol and the like; and copolymers such as those of polystyrene containing copolymers of butadiene and styrene and those formed by the copolymerization of acrylonitrile, butadiene and/or styrene.

Other materials which can be stabilized by the compounds of the present invention include lubricating oil of the aliphatic ester type, i.e., ethylene diazelate, pentaerythrityl tetracaproate, and the like; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, cutting fluids, waxes, resins, and the like; salts of fatty acids such as soaps and the like; and alkylene glycols, e.g., 2-methoxyethanol, 2-(2-methoxyethoxy)ethanol, triethylene glycol, octaethylene glycol, dibutylene glycol, dipropylene glycol and the like.

The compounds of this invention are particularly useful as UV light stabilizers, especially for the protection of polyolefins, for instance, polyethylene, polypropylene, poly-1-butene, poly-1-pentene, poly-3-methyl-1-butene, poly-4-methyl-1-pentene, various ethylene-propylene copolymers and the like.

In general, the stabilizers of this invention are employed from about 0.01 to about 5% by weight of the stabilized composition, although this will vary with the particular substrate and application. An advantageous range is from about 0.05 to about 2% and especially 0.1 to about 1%.

For addition to polymeric substrates, the stabilizers can be blended before polymerization or after polymerization, during the usual processing operations, for example, by hot-milling, the composition then being extruded, pressed, blow molded or the like into films, fibers, filaments, hollow spheres and the like. The heat stabilizing properties of these compounds may advantageously stabilize the polymer against degradation during such processing at the high temperature generally encountered. The stabilizers can also be dissolved in suitable solvents and sprayed on the surface of films, fabrics, filaments or the like to provide effective stabilization. Where the polymer is prepared from a liquid monomer as in the case of styrene, the stabilizer may be dispersed or dissolved in the monomer prior to polymerization or curing.

These compounds can also be used in combination with other additives such as antioxidants, sulfur-containing esters such as distearyl-$\beta$-thiodipropionate (DSTDP), dilauryl-$\beta$-thiodipropionate (DLTDP) in an amount of from 0.01 to 2% by weight of the organic material, and the like, pourpoint depressants, corrosion and rust inhibitors, dispersing agents, demulsifiers, antifoaming agents, fillers such as glass or other fibers, carbon black, accelerators and other chemicals used in rubber compounding, plasticizers, color stabilizers, di- and tri-alkyl- and -alkylphenyl-phosphites, as well as other phosphites, e.g., distearyl pentaerythritol diphosphite, heat stabilizers, ultraviolet light stabilizers, antiozonants, dyes, pigments, metal chelating agents, dyesites and the like. Often combinations with other additives such as those mentioned above, particularly the sulfur containing esters, the phosphites and/or the ultraviolet light stabilizers, will produce superior results in certain applications compared with those expected by the properties of the individual components.

The following formula represents co-stabilizers which are in certain instances very useful in combination with the stabilizers of this invention:

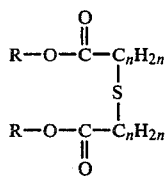

wherein R is an alkyl group having from 6 to 24 carbon atoms; and n is an integer from 1 to 6. Especially useful compounds of these are dilauryl-$\beta$-thiodipropionate and distearyl-$\beta$-thiodipropionate. The above co-stabilizers are used in the amount of from 0.01 to 2% by weight of the organic material, and preferably from 0.1 to 1%.

Although the compounds of this invention may be some degree also be effective as thermal stabilizers, if the processing of the polymer is carried out at high temperatures it is advantageous to incorporate additional antioxidants.

In most applications, it is desirable to incorporate into the resin composition, sufficient thermal antioxidants to protect the plastic against thermal and oxidative degradation. The amount of antioxidant required will be comparable to that of the actinic stabilizer. Namely, from about 0.005% to 5% and preferably from 0.01% to 2% by weight. Representative of such antioxidants are phosphite esters, such as triphenylphosphite and dibutylphosphite and alkyl arylphosphites such as dibutylphenylphosphite, and the like.

The best results have been obtained with the preferred class of thermal antioxidants, the hindered phenols. These compounds have been found to provide the best thermal stabilization with the least discoloration in the compositions of the invention. Among these phenolic antioxidants are included the following:

di-n-octadecyl(3-tert-butyl-4-hydroxy-5-methylbenzyl)-malonate
2,6-di-tert-butylphenol
2,2'-methylene-bis(6-tert-butyl-4-methylphenol)
2,6-di-tert-butylhydroquinone
octadecyl-(3,5-di-tert-butyl-4-hydroxybenzylthio)acetate
1,1,3-tris(3-tert-butyl-6-methyl-4-hydroxyphenyl)butane
1,4-bis(3,5-di-tert-butyl-4-hydroxybenzyl)2,3-5,6-tetramethylbenzene
2,4-bis(3,5-di-tert-butyl-4-hydroxyphenoxy)-6-(n-octylthio)-1,3,5-triazine
2,4-bis-(4-hydroxy-3,5-di-tert-butylphenoxy)-6-(n-octylthioethylthio)-1,3,5-triazine
2,4-bis-(n-octylthio)-6-(3,5-di-tert-butyl-4-hydroxyanilino)-1,3,5-triazine
2,4,6-tris-(4-hydroxy-3,5-di-tert-butylphenoxy)-1,3,5-triazine
n-octadecyl-3-(3,5-di-tert-butyl-4-hydroxyphenyl)propionate
n-octadecyl-3,5-di-tert-butyl-4-hydroxybenzoate
2-(n-octylthio)ethyl-3,5-di-tert-butyl-4-hydroxybenzoate
n-octadecanoyl-di-2-[3-(3,5-di-tert-butyl-4-hydroxyphenyl)propionyloxy]ethylamine
1,2-propylene di-[3-(3,5-di-tert-butyl-4-hydroxyphenyl)propionate]
pentaerythrityl tetra [3-(3,5-di-tert-butyl-4-hydroxyphenyl)propionate]
di-octadecyl-(3,5-di-tert-butyl-4-hydroxy-benzyl)phosphonate
di-octadecyl-1-(3,5-di-tert-butyl-4-hydroxyphenyl)ethanephosphonate The above phenolic hydrocarbon stabilizers are known and many are commercially available.

The above antioxidants have been listed only for the purpose of illustration and it is important to note that any other antioxidant can be employed with similar improved results. The above exemplified antioxidants and other related antioxidants which are incorporated herein by reference, are disclosed in greater detail in the following patents: Netherlands Patent Specification No. 67/1119, issued Feb. 19, 1968; Netherlands Patent Specification No. 68/03498 issued Sept. 18, 1968; U.S. Pat. Nos. 3,255,191; 3,330,859; 3,644,482; 3,281,505; 3,531,483; 3,285,855; 3,364,250; 3,368,997; 3,356,944 and 3,758,549.

The compounds of this invention may be prepared by reacting a piperidinol of the formula

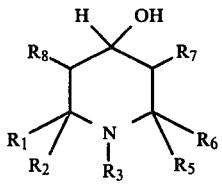

wherein $R_1$, $R_2$, $R_3$, $R_5$, $R_6$, $R_7$, and $R_8$ are as defined above in formula I, with an acid anhydride of the formula

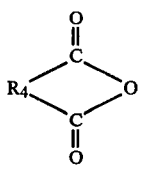

wherein $R_4$ is as defined above. In the case of 1,3 and 1,4-phenylene, the compounds may be prepared by reacting the piperidinol II with isophthalic or terephthalic acid via usual esterification procedures.

An alternative procedure in the preparation of the compounds of this invention is the reaction of the piperidinol II with a diacid of the formula

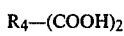

$R_4$—(COOH)$_2$                                        IV wherein R$_4$ is as defined above.

The acids and acid anhydrides which are reacted with the compounds of formula II may be prepared by methods well known in the art.

The metal salts of the present invention can be prepared by treating the hindered piperidine carboxylic acids of formula I with a reactive form of the metal or metal complex, e.g., sodium hydroxide or the like. Alternatively, and preferably in the case of metal complexes and metals other than the alkali metals, a double decomposition is employed. Thus for example, a sodium salt of the present invention is treated with nickel chloride. In a similar fashion use of other halides such as manganese dichloride, barium chloride and the like results in formation of the corresponding metal derivative.

The compounds of formula II may be prepared similarly to procedures presented in the published German Patent Application DT-OS No. 2,352,658, especially by reducing a corresponding 4-piperidone by catalytic hydrogenation or, e.g., with lithium aluminum hydride. The corresponding 4-ketone can be prepared by reacting an aliphatic ketone, this being a higher homologue of acetone, with ammonia, e.g., 2,3,6-trimethyl-2,6-diethyl-4-oxo-piperidine is obtained from methylethylketone and ammonia, similar to W. Traube in Chem. Ber. 41 (1908), 777. The corresponding 4-ketone can also be obtained by hydrolysis of an alkyl-substituted tetrahydropyridine in the presence of an acidic catalyst, similar to U.S. Pat. No. 3,513,170. Corresponding 4-ketones having different substituents in the 2- and 6-positions can be obtained by reacting first a ketone R$_5$—CO—R$_6$ with ammonia and hydrolyzing the formed pyrimidine derivative to give an amino ketone NH$_2$—C(R$_5$R$_6$)—CH(R$_7$)—CO—CH$_2$R$_8$ as described in Helv. Chim. Acta 30 (1947), 1114. In a second step, this amino ketone is reacted with ammonia and a second ketone R$_1$—CO—R$_2$, resulting in a pyrimidine derivative as described in Monatshefte Chemie 88 (1957), 464. From this the 4-ketone can be obtained by hydrolysis. Similar methods in preparing alkylated 4-piperidones are described in published German Patent Applications Nos. 2,429,745; 2,429,746; 2,429,935; 2,429,936 and 2,429,937.

Compounds of the type wherein both R$_1$ and R$_2$ and R$_5$ and R$_6$ together with the carbons to which they are attached form cyclohexyl or cyclopentyl rings can be prepared by the method of T. Yoshioka, S. Higashida and K. Murayama, Bull. Chem. Soc. Japan 45 636–638 (1972) with subsequent reduction of the ketone with hydrogen and a catalyst or sodium borohydride to the alcohol.

Compounds of formula I with R$_3$ being acyl may be prepared by acylation of the corresponding N—H compounds with the corresponding carboxylic acid, anhydride, ester or halide as known per se.

The following examples, presented for illustration and not limitation, will further serve to typify the nature of the present invention.

EXAMPLE 1

2,6-Diethyl-2,3,6-trimethyl piperidin-4-ol

In a 2-liter, 3-necked flask equipped with a stirrer, condenser, thermometer and nitrogen inlet were placed 197.3 g (1.0 moles) of 2,6-diethyl-2,3,6-trimethyl piperidin-4-one, 500 ml of 2 N sodium hydroxide and 500 ml of absolute ethanol. To the stirred reaction mixture, maintained under nitrogen, was added portionwise 18.92 m (0.5 moles) of sodium borohydride over a 1½ hour period. The reaction mixture was then stirred overnight at room temperature. The reaction mixture was decanted into a 4-liter separatory funnel and 2 liters of water were added. The aqueous layer was separated and the organic layer diluted with 500 ml of ether. The ether solution was washed with 2×1 l water. The first aqueous layer was extracted with 2×50 ml of ether, then the combined ether extracts were washed with 500 ml of water. The ether layers were combined, dried over 4A molecular sieves and evaporated under reduced pressure, giving 187.4 g of the desired 2,6-diethyl-2,3,6-trimethyl piperidin-4-ol which was purified further by vacuum distillation, b.p. 111°–115°/6 mm.

EXAMPLE 2

O-mono-(2',6'-diethyl-2',3',6'-trimethylpiperidyl-4')2-n-octylsuccinate

In a 1-liter, 3-necked flask equipped with a stirrer, thermometer, condenser and nitrogen inlet were placed 63.69 g (0.3 moles) of 2-n-octylsuccinic anhydride, 300 ml of VM&P Naphtha (an aliphatic hydrocarbon solvent, b.p. 120°–140°) and 59.79 g (0.3 moles) of 2,6-diethyl-2,3,6-trimethyl piperidin-4-ol. The reaction mixture was heated to reflux for 3 hours, then cooled to room temperature, at which time a gel formed in the reaction flask. The reaction mixture was transferred to a 1-necked resin flask and evaporated under vacuum at 100° C. to constant weight, giving, after cooling, 126.8 g of the desired half ester as a dark brown glass, which was characterized by the following analyses:

Elemental Analysis: Calculated for C$_{24}$H$_{45}$NO$_4$ F.W. 411.61: Calculated: C, 70.03; H, 11.02; N, 3.40. Found: C, 69.93; H, 10.90; N, 3.67.

EXAMPLE 3

Ni(II) Bis[O-mono(2',6'-diethyl-2',3',6'-trimethyl piperidyl-4')2-n-octyl succinate]

In a 300 ml, 3-necked flask equipped with a stirrer, nitrogen inlet, air condenser and dropping funnel were placed 20.58 g (0.05 moles) of O-mono-2',6'-diethyl-2',3',6'-trimethyl piperidyl-4')2-n-octyl succinate, 100 ml of water, and 25 ml of 2 N NaOH (0.05 moles). The reaction mixture was stirred until solution was complete (1½ hours), then a solution of 5.94 g (0.05 moles) of NiCl$_2$.6H$_2$O in 25 ml of water was added dropwise over a 10-minute period to the stirred solution. A copious green precipitate formed immediately. The reaction mixture was allowed to stir for 1 hour. Then 150 ml of ether was added with vigorous stirring. The reaction mixture was transferred to a separatory funnel, and the aqueous layer separated. The organic layer was washed with 200 ml of water and dried over 4 A molecular sieves. The ether solution was filtered and evaporated to dryness, giving 19.8 g of the desired Ni salt as a green glass.

EXAMPLE 4

Zn(II) Bis[O-mono(2',6'-diethyl-2',3',6'-trimethyl piperidyl-4')2-n-octyl succinate]

In a 300 ml, 3-necked flask equipped with a stirrer, nitrogen inlet, air condenser and dropping funnel were placed 20.58 g (0.05 moles) of O-mono-2',6'-diethyl-2',3',6'-trimethyl piperidyl-4')2-n-octyl succinate, 100 ml of water, and 25 ml of 2 N NaOH (0.05 moles). The reaction mixture was stirred until solution was complete (1½ hours), and then 12.17 ml of a 2.055 N solution of $ZnCl_2$ in $H_2O$ was added dropwise over a 10-minute period to the stirred solution. A copious gummy precipitate formed immediately. The reaction mixture was stirred vigorously for 1½ hours, then the aqueous layer was decanted from the gummy precipitate. The precipitate was dissolved in 500 ml of chloroform and the chloroform solution washed with 2×250 ml of water, and dried over 4 A molecular sieves. The chloroform solution was evaporated to dryness, giving 19.2 g of the desired Zn salt as a tacky brown glass.

EXAMPLE 5

By following the procedure of Example 3 and substituting for the $NiCl_2.6H_2O$ an equivalent amount of the following metal chlorides:
(a) $MgCl_2.6H_2O$
(b) $CoCl_2.6H_2O$
(c) $CaCl_2$
there was produced the following metal salts:
(a) Mg(II) Bis[O-mono(2',6'-diethyl-2',3',6'-trimethyl-piperidyl-4')2-n-octyl succinate], a tan, gummy solid.
(b) Co(II) Bis[O-mono(2',6'-diethyl-2',3',6'-trimethyl-piperidyl-4')2-n-octyl succinate], a purple glass.
(c) Ca(II) Bis[O-mono(2',6'-diethyl-2',3',6+-trimethyl-piperidyl-4')2-n-octyl succinate], a tan, tacky glass.

EXAMPLE 6

O-mono(2',6'-diethyl-2',3',6'-trimethyl piperidyl-4')2-n-octadecen-2''-yl-succinate By following the procedure of Example 2 and substituting for the 2-n-octyl succinic anhydride an equivalent amount of 2-n-octadecen-2'-yl succinic anhydride is produced the above-named half ester.

EXAMPLE 7

By following the procedure of Example 2 and substituting for the 2-n-octyl succinic anhydride an equivalent amount of the following anhydrides:
(a) cyclohexane 1,2-dicarboxylic anhydride
(b) bicyclo[2.2.1]hept-5-ene-1,2-dicarboxylic anhydride
there are produced the following half esters:
(a) O-mono(2',6'-diethyl-2',3',6'-trimethylpiperidyl-4')cyclohexane-1,2-dicarboxylate
(b) O-mono(2',6'-diethyl-2',3',6'-trimethylpiperidyl-4')bicyclo[2.2.1]hept-5-ene-2,3-dicarboxylate.

EXAMPLE 8

By following the procedure of Example 3 and substituting for the O-mono(2',6'-diethyl-2',3',6'-trimethyl piperidyl-4')2-n-octyl succinate and the $NiCl_2.6H_2O$ equivalent amounts of:
(a) O-mono(2',6'-diethyl-2',3',6'-trimethyl piperidyl-4')2-n-octadecen-2''-yl succinate + $CoCl_2.6H_2O$
(b) O-mono(2',6'-diethyl-2',3',6'-trimethyl piperidyl-4')cyclohexane 1,2-dicarboxylate + $MgCl_2.6H_2O$
(c) O-mono(2',6'-diethyl-2',3',6'-trimethyl piperidyl-4')bicyclo[2.2.1]hept-5-ene-1,2-dicarboxylate + $NiCl_2.6H_2O$
there are produced the following metal salts:
(a) Co(II) Bis[O-mono(2',6'-diethyl-2',3',6'-trimethyl piperidyl-4')2-n-octadecen-2''-yl succinate]
(b) Mg(II) Bis[O-mono(2',6'-diethyl-2',3',6'-trimethyl piperidyl-4')cyclohexane-1,2-dicarboxylate]
(c) Ni(II) Bis [O-mono(2',6'-diethyl-2',3',6'-trimethyl piperidyl-4')bicyclo[2.2.1]hept-5-ene-2,3-dicarboxylate].

EXAMPLE 9

Artificial Light Exposure Test

Deterioration of most polymers caused by ultraviolet light is so slow at ambient temperatures, even in the absence of stabilizers, that testing of the effects of stabilizers generally must be conducted either at higher temperatures or in an accelerated artificial light exposure device in order to yield results in a convenient period of time. The tests conducted on polymers using an artificial light exposure device is described below:

(a) Sample Preparation 5 mil Film—Unstabilized polypropylene powder (Hercules Profax 6501) is thoroughly blended with 0.5% by weight of O-mono(2',6'-diethyl-2',3',6'-trimethyl piperidyl-4)-2-n-octyl succinate and 0.2% by weight of dioctadecyl 3,5-di-t-butyl-4-hydroxybenzyl-phosphonate. The blended material is then milled on a two roll mill for 5 minutes at 182° C. The milled sheet is then compression molded at 220° C. into 5 mil thick film under a pressure of 175 psi and water cooled in the press.

(b) Testing Method

This test is conducted in a FS/BL unit, basically of the American Cyanamid design, which consists of 40 tubes of alternating fluorescent sunlamps and black lights (20 of each). The 5 mil sample film which are mounted on 3"×2" IR card holders with ¼"×1" windows are placed on a rotating drum 2 inches from the bulbs in the FS/BL unit. The time in hours is noted for the development of 0.5 carbonyl absorbance units as determined on an Infrared Spectophotometer. The development of carbonyl functional groups in the polymer is proportional to the amount of degradation caused by the ultraviolet light exposure.

Polypropylene stabilized with the above hindered piperidine compound is found to be much more stable than the unstabilized polypropylene. Polypropylene is likewise stabilized when the following stabilizers are substituted for O-mono(2',6'-diethyl-2',3',6'-trimethyl piperidyl-4')2-n-octyl succinate in the procedures described above:
(a) Ni(II) Bis [O-mono(2',6'-diethyl-2',3',6'-trimethyl piperidyl-4')2-n-octyl succinate]
(b) Zn(II) Bis [O-mono(2',6'-diethyl-2',3',6'-trimethyl piperidyl-4')2-n-octyl succinate]
(c) Mg(II) Bis [O-mono(2',6'-diethyl-2',3',6'-trimethyl piperidyl-4')2-n-octyl succinate]
(d) Co(II) Bis [O-mono(2',6'-diethyl-2',3',6'-trimethyl piperidyl-4')2-n-octyl succinate]
(e) Ca(II) Bis [O-mono(2',6'-diethyl-2',3',6'-trimethyl piperidyl-4')2-n-octyl succinate]
(f) O-mono(2',6'-diethyl-2',3',6'-trimethyl piperidyl-4')cyclohexane-1,2-dicarboxylate
(g) Ni(II) Bis [O-mono(2',6'-diethyl-1',2',3',6'-tetramethyl piperidyl-4')2-n-octyl succinate]
(h) Ni(II) Bis [O-mono(2',6'-diethyl-2',3',6'-trimethyl piperidyl-4')bicyclo[2.2.1]hept-5-ene-2,3-dicarboxylate]
(i) Co(II) Bis [O-mono(2',6'-diethyl-2',3',6'-trimethyl piperidyl-4')2-n-octadecen-2''-yl succinate]
(j) Ni(II) Bis [O-mono(2',6'-di-n-butyl-2',6'-dimethyl-3'-n-propyl piperidyl-4')2-n-octadecen-2''-yl succinate]

Other hindered phenolic antioxidants may be used in place of di-octadecyl(3,5-di-t-butyl-4-hydroxybenzyl)- phosphonate in the above mentioned compositions, for example, di-n-octadecyl α-(3-t-butyl-4-hydroxy-4-methylbenzyl)malonate, 2,4-bis-(n-octylthio)-6-(3,4-di-t-butyl-4-hydroxyaniline)-1,3,5-triazine, octadecyl 3-(3',5'-di-t-butyl-4'-hydroxyphenyl)propionate, pentaerythritol-tetrakis[3-(3,5-di-t-butyl-4-hydroxyphenyl)]-propionate, tris-(3,5-di-t-butyl-4-hydroxybenzyl)isocyanurate, 2,6-di-tert-butyl-4-methylphenol, N,N,N-tris-(3,5-di-tert-butyl-4-hydroxybenzyl)isocyanurate, and 2,4,6-tris(3,5-di-tert-butyl-4-hydroxybenzyl)-1,3,5-trimethylbenzyl.

The above compositions are also stabilized when the following UV absorbers are included in the formulation at 0.01 to 2%:

(a) 2(2'-hydroxy-3',5'-di-t-butylphenyl)-5-chlorobenzotriazole
(b) 2-hydroxy-4-methoxy-5-sulfobenzophenone trihydrate
(c) 2-hydroxy-4-n-octoxybenzophenone
(d) [2,2'-thiobis(4-t-octylphenolate)]-n-butylamine nickel II
(e) p-octylphenyl salicylate
(f) 2,2'-dihydroxy-4-4'-dimethoxybenzophenone
(g) 2(2'-hydroxy-5'-methylphenyl)-benzotriazole.

EXAMPLE 10

High impact polystyrene resin containing elastomer (i.e., butadiene-styrene) is stabilized against loss of elongation properties due to exposure to ultraviolet light by incorporation of 0.2% by weight of O-mono(2',6'-diethyl-2',3',6'-trimethyl piperidyl-4')2-n-octyl succinate.

The unstabilized resin is dissolved in chloroform and the stabilizer then added, after which the mixture is cast on a glass plate and the solvent evaporated to yield a uniform film which, upon drying, is removed and cut up, and then pressed for 7 minutes at a temperature of 163° C. and a pressure of 2,000 pounds per square inch into sheet of uniform thickness (25 mil). The sheets are then cut into strips approximately 4×0.5 inches. A portion of these strips is then measured for percent of elongation in the Instron Tensile Testing Apparatus (Instron Engineering Corporation, Quincy, Mass.). The remaining portions of the strips are placed in an FS/BL chamber according to Example 6(B) except that the sameple are mounted and white cardboard stock and the time to 50% reduction in elongation is measured. The stabilized polystyrene resin retains its elongation property longer than the unstabilized resin.

EXAMPLE 11

Unstabilized linear polyethylene is solvent blended in methylene chloride with 0.5% by weight of the substrate of the nickel complex of O-mono(2',6'-diethyl-2',3',6'-trimethyl piperidyl-4')2-n-octyl succinate and then vacuum dried. The resin is then extrusion compounded on a 1 inch 24/1=L/D extruder, melt temperature 450° F. (232° C.) and pressed for 7 minutes at a temperature of 163° C. and a pressure of 2,000 psi into a sheet of uniform thickness of 100 mil. The sheets are then cut into plaques of 2 inch×2 inch. The plaques are then exposed in an FS/BL exposure device and color measurements made periodically using a Hunter Color Difference Meter Model D25. Polyethylene stabilized with the above compound is found to be much more stable than the unstabilized polyethylene or the polyethylene stabilized only with an antioxidant.

EXAMPLE 12

A quantity of SBR emulsion containing 100 g of rubber (500 ml of 20% SBR obtained from Texas U.S., Synpol 1500) previously stored under nitrogen, is placed in a beaker and stirred vigorously. The pH of the emulsion is adjusted to 10.5 with a 0.5 N NaOH solution.

To the emulsion is added 50 ml of 25% NACl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for ½ hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (>1 mm) at 40°-45° C.

The dried rubber (25 g) is heated under nitrogen at 125° C. in a Brabender mixer and to this is added with mixing 0.25 g (0.5%) of Co(II) bis[O-mono(2',6'-diethyl-2',3',6'-trimethylpiperidyl-4')2-n-octyl succinate]. The composition is mixed for 5 minutes after which it is cooled and compression molded at 125° C. into 5"×0.025" plaques.

The plaques are exposed to an Xenon Arc weatherometer and the color measurement (L-b) is made after 45, 125 and 290 hours. The samples stabilized with the above compound are found to be much more light stable than the unstabilized samples.

EXAMPLE 13

The 50 g of polyacetal resin containing 0.1% of an acid scavenger, dicyandiamide, is added 0.2% by weight of Ca(II) bis[O-mono(2',6'-diethyl-2',3',6'-trimethylpiperidyl-4')-2-n-octyl succinate and milled for 7 minutes at 200° C. in a Brabender Plasti-recorder. The milled formulation is subsequently pressed into a 40 mil sheet at 215° C. at 350 psi for 90 seconds then cooled quickly in a cold press at 350 psi. The stabilized sheets are then remolded for 2 minutes at contact pressure and for 3 minutes at 300 psi at 215° C. to give plaques 1½ inch×2½ inch×125 mil. Thereafter, the testing procedure of Example 10 is followed to determine the light stability of the samples. The stabilized samples are found to be much more stable than the unstabilized samples.

EXAMPLE 14

Unstabilized thoroughly dried polyethylene terphthalate chips are dry blended with 1.0% of ZN(II) bis-[O-mono(2',6'-diethyl-2',3',6'-trimethylpiperidyl-4')2-n-octyl succinate]. 60/10 denier multifilament is melt spun at a melt temperature of 290° C. The oriented fiber is wound on white cards and exposed in an Xenon Arc Fadeometer. Color measurements are made periodically with a Hunter Color Difference Meter Model D25. The stabilized samples are found to be much more light stable than the unstabilized samples.

EXAMPLE 15

(a) A composition comprising acrylonitrilebutadienestyrene terpolymer and 1% by weight of O-mono(2',6'- diethyl-2',3',6'-trimethylpiperidyl-4')2-n-octadecenyl succinate resists embrittlement due to exposure to ultraviolet light longer than one which does not contain the stabilizer.

(b) A composition comprising polyurethane prepared from toluene diisocyanate and alkylene polyols and 1.0% by weight of Ni(II) bis[O-mono-2',6'-diethyl-2',3',6'-trimethylpiperidyl-4')cyclohexane-1,2-dicarboxylate is more stable to sunlight, fluorescent sunlamps, black lights and fluorescent lights than the unformulated polyurethane.

(c) A composition comprising a polycarbonate prepared from bisphenol-A and phosgene and 1% by weight of Ni(II) bis[O-mono(2',6'-diethyl-2',3',6'-trimethylpiperidyl-4')2-n-octadecen-2"-yl succinate] resists discoloration due to exposure to ultraviolet light longer than one which does not contain the stabilizer.

(d) A composition comprising polymethylmethacrylate and 0.25% by weight of O-mono(2',6'-diethyl-2',3',6'-trimethylpiperidyl-4')2-n-octadecen-2"-yl succinate resists discoloration due to exposure to ultraviolet light longer than one which does not contain the stabilizer.

EXAMPLE 16

(a) A stabilized polyamide (nylon 6,6) is prepared by incorporating therein 0.1% of Ni(II) bis[O-mono(2',6'-diethyl-2',3',6'-trimethylpiperidyl-4')-phthalate]. The light stability of the stabilized composition is superior to that of an unstabilized polyamide.

(b) A stabilized polyphenylene oxide polymer (prepared by polymerizing 2,6-dimethylphenol is prepared by incorporating therein 0.5% by weight of Ni(II)bis[O-mono(2',6'-diethyl-2',3',6'-trimethylpiperidyl-4')cyclohex-4-ene-1,2-dicarboxylate]. The stabilized compositions resist embrittlement due to exposure to ultraviolet light longer than one which does not contain the stabilizer.

(c) A stabilized crystalline polystyrene is prepared by incorporating therein 0.1% weight of Ni(II)bis[O-mono(2',6'-di-n-butyl-2',6'-dimethyl-3'-n-propyl-piperidyl-4')2-n-octadecen-2"-yl succinate]. The stabilized composition resists embrittlement due to exposure to ultraviolet light longer than one which does not contain the stabilizer.

Antioxidants may also be incorporated into each of the above mentioned compositions, for example, di-n-octadecyl-α,α'-bis(3-butyl-4-hydroxy-5-methylbenzyl)-malonate 2,4-bis(4-hydroxy-3,5-di-t-butylphenoxy)-6-(n-octylthioethylthio)-1,3,5-triazine, 2,4-bis(3,5-di-t-butyl-hydroxyphenoxy)-6-(n-octylthio-1,3,5-triazine di-n-octadecyl 3(3',5'-di-t-butyl-4-hydroxyphenyl)propionate, respectively.

The invention encompasses compounds having the formula

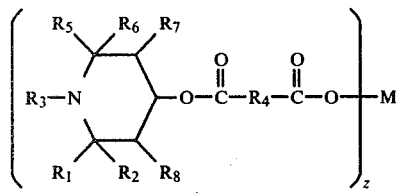

In the above structure M is hydrogen or a metal and may also be $M'(R)_n$ where R represents water, alcohols, glycols, diols, triols, tetraols, pentols, hexitols as well as ammonia, amines and amino alcohols. M' is a metal. In the case of M',z represents the primary value and n represents the coordination number of the metals.

The compounds wherein M is $M'(R)_n$ may be prepared by mixing equimolar ratios of the compounds containing M and the co-ligand R in an appropriate solvent, refluxing, and subsequently evaporating to dryness. More specifically, when M is Nickel or R is n-butylamine the compound may be suspended in isopropanol, the n-butylamine added, and the mixture refluxed until solution is achieved, then evaporated to dryness.

What is claimed is:

1. A compound of the formula

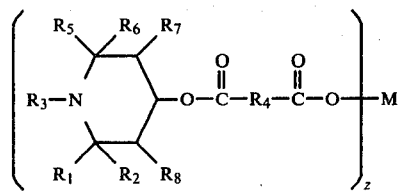

wherein
$R_1$ and $R_2$ independently of each other are straight- or branched-chain alkyl having from 1 to 6 carbon atoms, or together with the carbon to which they are bound form a cyclopentyl or cyclohexyl ring, which is unsubstituted or substituted with a methyl group, $R_3$ is hydrogen, alkyl having 1 to 12 carbon atoms, β-methoxyethyl, alkenyl having 3 to 4 carbon atoms, propargyl, benzyl, or alkyl substituted benzyl, or acyl, $R_4$ is 1,2-cycloalkylene or 1,2-cycloalkenylene having 4 to 6 carbon atoms, 2,3-bicycloalkylene or 2,3-bicycloalkenylene having 7 to 8 carbon atoms or 1,2- 1,3- or 1,4-phenylene, M is hydrogen or a metal selected from the group consisting of barium, calcium, magnesium, sodium, and potassium, z has a value of from 1 to 4, the value of z being the same as the available valence of M, and either (a) $R_5$ is alkyl of 2 to 6 carbon atoms, $R_6$ is alkyl of 1 to 6 carbon atoms, and $R_7$ and $R_8$ are independently hydrogen or alkyl of 1 to 5 carbon atoms, provided that $R_7$ and $R_8$ are not both hydrogen, or (b) $R_5$ and $R_6$ together with the carbon to which they are bound form a cyclopentyl or cyclohexyl ring, which is unsubstituted or substituted with a metyl group and $R_7$ and $R_8$ are independently hydrogen or alkyl of 1 to 5 carbon atoms.

2. A compound according to claim 1 wherein $R_1$ is straight- or branched-chain alkyl of 1 to 6 carbon atoms, $R_2$ is straight- or branched-chain alkyl of 2 to 6 carbon atoms, $R_5$ is alkyl of 2 to 6 carbon atoms, $R_6$ is alkyl of 1 to 6 carbon atoms, and $R_7$ and $R_8$ are independently hydrogen or alkyl of 1 to 5 carbon atoms, provided that $R_7$ and $R_8$ are not both hydrogen.

3. A compound according to claim 1 wherein $R_1$ and $R_6$ are methyl, $R_5$ is alkyl of 2 to 6 carbon atoms, $R_6$ is alkyl of 1 to 6 carbon atoms, and $R_7$ and $R_8$ are independently hydrogen or alkyl of 1 to 5 carbon atoms, provided that $R_7$ and $R_8$ are not both hydrogen.

4. A compound according to claim 1 wherein $R_4$ is 1,2-cycloalkylene or 1,2-cycloalkylene having 4 to 6 carbon atoms.

5. A compound according to claim 1 wherein R$_4$ is 2,3-bicycloalkylene or 2,3-bicycloalkylene having 7 to 8 carbon atoms.

6. A compound according to claim 1 wherein R$_4$ is 1,2-, 1,3- or 1,4-phenylene.

7. A compound according to claim 2 wherein M is selected from hydrogen.

8. A compound according to claim 1 which is O-mono(2',6'-diethyl-2',3',6'-trimethylpiperidyl-4')cyclohexane-1,2-dicarboxylate.

9. A composition of matter stabilized against ultraviolet deterioration which comprises a synthetic organic polymer normally subject to ultraviolet deterioration containing from
   (a) 0.005% to 5% of a stabilizing compound according to Claim 1
   (b) 0 to 5% of a phenolic antioxidant,
   (c) 0 to 5% of a thio co-stabilizer, and
   (d) 0 to 5% of a U.V. absorber.

10. A composition of matter stabilized against ultraviolet deterioration which comprises a synthetic organic polymer normally subject to ultraviolet deterioration containing from
    (a) 0.005% to 5% of a stabilizing compound according to claim 1,
    (b) 0 to 5% of a phenolic antioxidant,
    (c) 0 to 5% of a phosphite co-stabilizer, and
    (d) 0 to 5% of a U.V. absorber.

11. A composition of claim 9 wherein the organic material is a polyolefin.

12. A composition of claim 11 wherein the polyolefin is polypropylene.

* * * * *